United States Patent
Syms

(10) Patent No.: US 7,973,278 B2
(45) Date of Patent: *Jul. 5, 2011

(54) MICROENGINEERED IONISATION DEVICE

(75) Inventor: Richard Syms, London (GB)

(73) Assignee: Microsaic Systems Limited, Working (GB)

( * ) Notice: Subject to any disclaimer, the term of this patent is extended or adjusted under 35 U.S.C. 154(b) by 866 days.

This patent is subject to a terminal disclaimer.

(21) Appl. No.: 12/001,796

(22) Filed: Dec. 12, 2007

(65) Prior Publication Data

US 2010/0276588 A1 Nov. 4, 2010

(30) Foreign Application Priority Data

Dec. 19, 2006 (GB) .................................. 0625272.0

(51) Int. Cl.
*H01J 49/04* (2006.01)
*H01J 49/10* (2006.01)
*G21K 5/04* (2006.01)

(52) U.S. Cl. ...... 250/288; 250/281; 250/282; 250/423 R

(58) Field of Classification Search .................. 250/281, 250/282, 288, 423 R, 424, 425

See application file for complete search history.

(56) References Cited

U.S. PATENT DOCUMENTS

| | | | |
|---|---|---|---|
| 5,726,447 A | 3/1998 | Aisawa et al. | |
| 5,747,815 A * | 5/1998 | Young et al. | 250/423 R |
| 6,110,343 A | 8/2000 | Ramsey et al. | |
| 6,462,337 B1 | 10/2002 | Li et al. | |
| 7,115,861 B2 | 10/2006 | Livi | |
| 7,435,952 B2 * | 10/2008 | Finlay et al. | 250/292 |
| 7,615,744 B1 * | 11/2009 | Syms | 250/288 |
| 2002/0000516 A1 | 1/2002 | Schultz et al. | |
| 2005/0077897 A1 * | 4/2005 | Syms | 324/318 |
| 2005/0109948 A1 | 5/2005 | Park et al. | |
| 2005/0133713 A1 | 6/2005 | Brennen | |
| 2005/0263699 A1 | 12/2005 | Miller et al. | |
| 2006/0071161 A1 * | 4/2006 | Syms | 250/290 |
| 2006/0192108 A1 * | 8/2006 | Yeatman et al. | 250/288 |
| 2006/0255255 A1 * | 11/2006 | Miller et al. | 250/281 |
| 2007/0278399 A1 | 12/2007 | Kim et al. | |
| 2008/0001082 A1 * | 1/2008 | Syms et al. | 250/288 |

FOREIGN PATENT DOCUMENTS

| | | |
|---|---|---|
| GB | 2428514 | 1/2007 |
| WO | WO 98/35376 | 8/1998 |
| WO | WO 00/15321 | 3/2000 |

OTHER PUBLICATIONS

Gaskell, S.J., "Electrospray: Principles and Practice," *Journal of Mass Spectrometry*, vol. 32, 677-688 (1997).

(Continued)

*Primary Examiner* — Robert Kim
*Assistant Examiner* — Nicole Ippolito Rausch
(74) *Attorney, Agent, or Firm* — Bishop & Diehl, Ltd.

(57) ABSTRACT

This invention provides a method of aligning a capillary needle, a set of electrodes, and an input to a mass spectrometer. The electrode system is formed as an assembly of two separate chips and forms an ionization device. Each chip is formed on an insulating plastic substrate. The first chip carries mechanical alignment features for the capillary electrospray needle together with a set of partial electrodes. The second chip carries a set of partial electrodes. The complete electrode system is formed when the chips are assembled in a stacked configuration.

40 Claims, 13 Drawing Sheets

OTHER PUBLICATIONS

Abian, J., "The Coupling of Gas and Liquid Chromatography With Mass Spectrometry," *Journal of Mass Spectrometry*, vol. 34, 157-168 (1999).

Duffin, K.L. et al., "Atmospheric Pressure Ion-Sampling System for Liquid Chromatography/Mass Spectrometry Analyses on a Benchtop Mass Spectrometer," *Analytical Chemistry*, vol. 64, 61-68 (1992).

Lee, Edgar D. et al., "Thermally Assisted Electrospray Interface for Liquid Chromatography/Mass Spectrometry," *Rapid Communications in Mass Spectrometry*, vol. 6, 727-733 (1992).

Huggins, Thomas et al., "Capillary Electrophoresis/Mass Spectrometry Determination of Inorganic Ions Using an Ion Spray-Sheath Flow Interface," *Electrophoresis*, 14, 531-539 (1993).

Hirabayashi, Atsumu et al., "Charged Droplet Formation in Sonic Spray," *International Journal of Mass Spectrometry and Ion Processes*, 175, 277-282 (1998).

Wilm, Matthias et al., "Analytical Properties of the Nanoelectrospray Ion Source," *Analytical Chemistry*, vol. 68, 1-8 (1996).

Ramsey, R.S. et al., "Generating Electrospray from Microchip Devices Using Electroosmotic Pumping," *Analytical Chemistry*, vol. 69, 1174-1178 (1997).

Licklider, Larry et al., "A Micromachined Chip-Based Electrospray Source for Mass Spectrometry," *Analytical Chemistry*, vol. 72, 367-375 (2000).

Svedberg, Malin et al., "Sheathless Electrospray from Polymer Microchips," *Analytical Chemistry*, vol. 75, 3934-3940.

LeGac, Severine et al., "A Planar Microfabricated Nanoelectrospray Emitter Tip Based on a Capillary Slot," *Electrophoresis*, 24, 3640-3647 (2003).

Kameoka, Jun et al., "An Electrospray Ionization Source for Integration With Microfluidics," *Analytical Chemistry*, vol. 74, 5897-5901 (2002).

Schultz, Gary A. et al., "A Fully Integrated Monolithic Microchip Electrospray Device for Mass Spectrometry," *Analytical Chemistry*, vol. 72, 4058-4063 (2000).

Griss, Patrick et al., "Development of Micromachined Hollow Tips for Protein Analysis Based on Nanoelectrospray Ionization Mass Spectrometry," *Journal of Micromechanics and Microengineering*, 12, 682-687 (2002).

Bean, Kenneth E., "Anisotropic Etching of Silicon," (1978). *IEEE Transactions on Electron Devices*, vol. ED-25, No. 10, 1185-1193 (1978).

Hynes, A.M. et al., "Recent Advances in Silicon Etching for MEMS Using the ASE™ Process," *Sensors and Actuators*, vol. 74, 13-17 (1999).

Lorenz, H. et al., "SU-8: A Low-Cost Negative Resist for MEMS," *J. Micromech. Microeng.*, 7, 121-124 (1997).

G.A. Valsakovic et al., "Attomole-Sensitivity Electrospray Source for Large-Molecule Mass Spectrometry," *Analytical Chemistry*, vol. 67, 1995, pp. 3802-3805.

F. Xiang et al., "An Integrated Microfabricated Device for Dual Microdialysis and On-Line ESI-Ion Trap Mass Spectrometry for Analysis of Complex Biological Samples," *Analytical Chemistry*, vol. 71, No. 8, Apr. 15, 1999, pp. 1485-1490.

* cited by examiner

MICROENGINEERED IONISATION DEVICE

CROSS-REFERENCE TO RELATED APPLICATIONS

This application claims priority to Great Britain application No. GB0625272.0 filed Dec. 19, 2006 and is expressly incorporated herein by reference and made a part hereof.

FEDERALLY SPONSORED RESEARCH OR DEVELOPMENT

Not Applicable.

TECHNICAL FIELD

This invention relates to mass spectrometry, and in particular to the use of mass spectrometry in conjunction with liquid chromatography or capillary electrophoresis. The invention particularly relates to an ionisation device that is used to generate an ion spray for introduction into the mass spectrometer, the ionisation device being provided between a fluid source and the mass spectrometer and being integrally formed on a chip.

BACKGROUND OF THE INVENTION

Electrospray is a common method of soft ionisation in biochemical mass spectrometry (MS), since it allows the analysis of fluid samples pre-separated by liquid chromatography (LC), the ionization of complex molecules without fragmentation, and a reduction in the mass-to-charge ratio of heavy molecules by multiple charging [Gaskell 1997; Abian 1999]. It may be used in a similar way with fluid samples pre-separated by other methods such as capillary electrophoresis (CE).

The principle is simple. A voltage is applied between an electrode typically consisting of a diaphragm containing an orifice and a capillary needle containing the analyte. Liquid is extracted from the tip and drawn into a Taylor cone, from which large charged droplets are emitted. The droplets are accelerated to supersonic speed, evaporating as they travel. Coulomb repulsion of the charges in the shrinking droplet results in fragmentation to ions when the Rayleigh stability limit is reached. The resulting ions can be multiply charged.

An electrospray mass spectrometer system contains a number of key elements:
   An electrospray ionisation source capable of interfacing to an LC or CE system
   An interface to couple ions (in preference to molecules) into a vacuum chamber
   An alignment and/or observation system capable of maximising the coupling
   A mass filter and detector.

Conventionally, the spray is passed from atmospheric pressure via a chamber held at an intermediate pressure. Several vacuum interfaces that use differential pumping to match flow rates to achievable pressures have been developed [Duffin 1992]. The ion optics normally consist of input and output orifices such as capillaries, capillary arrays and skimmer electrodes, and occasionally also a quadrupole lens operating as an ion guide in all-pass mode. These components are used to maximise the ratio of coupled ions to neutrals, which would otherwise swamp the chamber.

Various methods are used to promote a well-dispersed spray of small droplets and hence a concentrated flow of analyte ions. Solvent can be preferentially driven off, by direct heating [Lee 1992]. Advantages may be obtained by the use of a nebuliser gas flow [Huggins 1993], and nebulisation may be enhanced by ultrasound [Hirabayashi 1998].

Alignment in electrospray is not critical, and the spray may simply be directed towards the MS input. Alternatively, an off-axis spray direction may be used to promote the separation of neutrals. Co-axial lenses mounted directly on the capillary have been developed to focus the spray [U.S. Pat. No. 6,462,337]; however, there are limits to the electrode complexity that can be achieved using such simple mechanical systems.

In a conventional electrospray system, with capillaries of $\approx 100$ µm internal diameter, flow rates are of the order of 1 µl min$^{-1}$, and extraction voltages lie in the range 2.5 kV-4 kV. Flow rates and voltages are considerably reduced in so-called "nanospray systems", based on capillaries having internal diameters ranging down to $\approx 10$ µm [Wilm 1996]. Such capillaries are relatively easy to fabricate, and are available with a range of diameters and frits. Decreasing the capillary diameter and lowering the flow rate also tends to create ions with higher mass-to-charge ratio, extending the applicability further towards biomolecules.

Because of the reduced size of the spray cone, the generation of a stable and well aligned spray from a nanospray source is more critical. Operation typically involves Because of the reduced size of the spray cone, the generation of a stable and well aligned spray from a nanospray source is more critical. Operation typically involves mounting the source on a micropositioner and using a video camera to observe the spray entering the vacuum inlet of an atmospheric pressure ionisation (API) mass spectrometer. Sources are sold customised for most popular brands of mass spectrometer. However, such systems are large, complex and costly.

To reduce costs, a variety of attempts have been made to integrate some of the components of nanospray ionisation sources. Ramsey and Ramsey [1997] showed that a spray could be drawn from the edge of a glass chip containing an etched capillary. Since then, integrated capillaries with in-plane flow have been demonstrated in many materials, especially plastics [Licklider 2000; Svedberg 2003]. In some cases, the fluid has been extracted from a slot rather than a channel [Le Gac 2003]; in others, from a shaped surface [Kameoka 2002]. Devices have also been formed in one-dimensional arrays. Geometries in which the flow is passed perpendicular to the surface of the chip have also been demonstrated, often by deep reactive ion etching of silicon [Schultz 2000; Griss 2002]. Such devices may be formed into two-dimensional arrays.

Almost exclusively, the advances above consist of attempts to integrate system sub-components leading up to the ion emitter. They concentrate on the fluidic part of the system, ignoring the problems of separating ions from neutrals, and of generating a stable ion spray that is well-aligned to the inlet to the vacuum system. As a result, they are not suitable for a low cost nanospray system, because accurate alignment still requires expensive positioning devices.

There is therefore a need to provide a low cost nanospray system.

SUMMARY OF THE INVENTION

The invention addresses these and other problems by providing a solution to the problems of alignment and electrode mounting in a low-cost nanospray source by using microelectromechanical systems technology to form appropriate mechanical alignment and conducting electrode features on insulating plastic substrates in an integrated manner. The approach also allows integration of features for fluid drainage, a nebuliser gas flow and spray heating and spray deflection.

This invention provides a method of aligning a nanospray capillary needle from a fluid source with a set of electrodes and providing an ion spray that is input to a mass spectrometer, such as an atmospheric pressure ionisation (API) spectrometer. The electrode system is formed using microelectromechanical systems or some other microengineering technology, as an assembly of at least two separate chips. Each chip is formed on an insulating plastic substrate. The first chip carries mechanical alignment features for the capillary electrospray needle together with a set of partial electrodes. The second chip carries a set of partial electrodes. The complete electrode system is formed when the chips are assembled in a stacked configuration, and consists of one or more electrodes forming components such as an einzel lens capable of initiating a Taylor cone and separating ions from neutrals by focusing.

Accordingly, the invention provides a system according to claim 1 with advantageous embodiments provided in the dependent claims thereto. The invention also provides a method of fabricating such a system as detailed in the main independent method claim.

These and other features will be better understood with reference to the following drawings.

DETAILED DESCRIPTION

Features of the invention will now be described with reference to FIGS. 1 to 9, which form part of an earlier application of the present applicant and is currently pending as Patent Application in United Kingdom No. 0519439.4, European Patent Application No. 06117211.0, Patent Application in Canada No. 2552086, Patent Application in Japan No. 2006-197964 and U.S. patent application Ser. No. 11/487,735 all of which are as of yet unpublished and are incorporated herein by way of reference. While the present invention shares many features with this earlier application other features are different, the specifics of which will become apparent through a reading of the following.

The present inventor has realised that the benefit of MEMS or other microengineered structures can be extended to nanospray applications. In MEMS, widely used methods of lithographic patterning, oxidation and metallisation are combined with specialised techniques such as anisotropic wet chemical etching [Bean 1978] and deep reactive ion etching [Hynes 1999] to form three-dimensional features in crystalline semiconductors such as silicon. UV exposure of specialised photosensitive polymers such as SU-8 may be used to form three-dimensional features in plastics [Lorenz 1997]. These methods may be used to combine insulating substrates, alignment features and conducting electrodes. The present inventor has realised that at least potentially, they may therefore form an integrated nanospray ionisation source at low cost. voltages, in a wet environment, so that electrical isolation and drainage are both required. The substrate material most commonly used in MEMS, silicon, is therefore not appropriate; however, other insulating materials such as glasses are difficult to micromachine. To obtain a stable spray, a closely-spaced electrode containing an axially aligned orifice is typically required. To obtain efficient ion separation from neutrals, electrostatic deflection or focusing is required. For focusing, further electrodes containing aligned orifices are needed. If the ion path is itself in the plane of a substrate, such orifices are extremely difficult to form by in plane patterning alone. Finally, it is desirable to integrate features capable of providing a gas flow around the spray, of promoting nebulisation, and of preferentially evaporating solvent. For these and other reasons there has heretofore not been possible an integrated MEMS nanospray system. However, as will be understood from a review of FIGS. 1 to 9 and FIGS. 10 to 13, the present inventor has addressed these and other issues.

Figure 1:
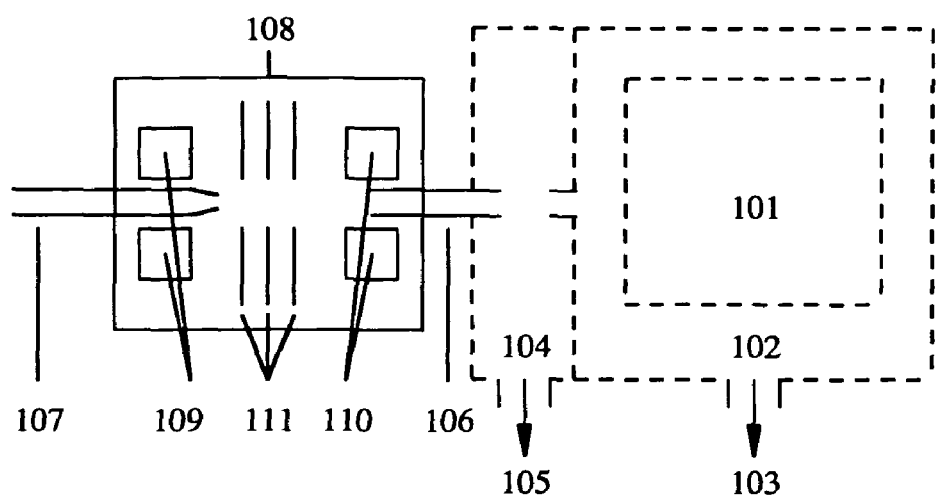
FIG. 1 shows in schematic form a microengineered nanospray system aligning a nanospray needle with the capillary input to an atmospheric pressure ionisation mass spectrometer according to an embodiment of the present invention.

FIG. 1 illustrates the concept of a microengineered nanospray electrode system. The system includes a mass spectrometer system 101 which is housed within a first 104 and a second vacuum chamber 102. The mass spectrometer 101 is provided in a high-vacuum enclosure 102 pumped (for example) by a turbomolecular pump 103. Ions are channelled into this chamber via a further chamber 104 held at an intermediate pressure and pumped (again, for example) by a rotary pump 105. The inlet to the vacuum system of this embodiment is assumed to be a capillary 106. The exact configuration of these components is not, it will be appreciated, important, and as will be understood with reference to a FIGS. 10 to 13, a nanospray electrode system according to the teaching of the invention could be used with any type of mass spectrometer system. For example, the filter element of the mass spectrometer could be an ion trap, a quadrupole, a magnetic sector, a crossed-field or a time of flight device. Equally, the intermediate vacuum chamber could contain a range of components including further capillaries and skimmer electrodes.

The mass spectrometer 101 is provided to perform analysis on an ion spray that is introduced into the mass spectrometer. In the embodiment of FIG. 1, this introduction is achieved using a capillary 106 which couples a generated spray into the mass spectrometer. According to the teaching of the invention, the ion spray is generated within an ion spray ionisation device 108 which is provided between the mass spectrometer and a fluid source.

In order to perform analysis within the mass spectrometer, the system of the invention takes a fluid from a fluid source, ionises that fluid to form an ion spray and then introduces that ion spray into the mass spectrometer. Within the context of the invention is provided an ionisation device 108 which is interfaced between the fluid source and the mass spectrometer. The overall input to the ionisation device 108 is provided in this example of FIG. 1 by a nanospray capillary 107. Within the embodiment of FIG. 1, the generated ion beam is then presented to the mass spectrometer using a capillary 106 which directly physically couples the ionisation device 108 and the mass spectrometer 101. In this way, a fluid enters the device 108 through a capillary and the generated ion beam exits the device 108 through a capillary. There is no exposure of the generated ion spray to the atmosphere prior to its introduction into the capillary 106 and transport into the mass spectrometer. Alignment between the nanospray capillary 107 and the capillary input to the mass spectrometer 106 is provided by the ionisation device provided on a microengineered chip 108. The chip contains a first set of mechanical alignment features 109 for the nanospray capillary and a second set of alignment features 110 for the capillary input to the mass spectrometer. The chip also contains a set of electrodes 111 set up perpendicular to the ion path, which may (for example, but not exclusively) consist of diaphragm electrodes. Other features may be integrated on the chip, including holes for drainage and gas inlet. Within this configuration, as the generated ion beam is already directed into the entry port to the mass spectrometer prior to exiting the ionisation device 108, there is a direct physical coupling between the exit port of the ionisation device 108 and the mass spectrometer 101 provided by the capillary needle 106.

Figure 2:
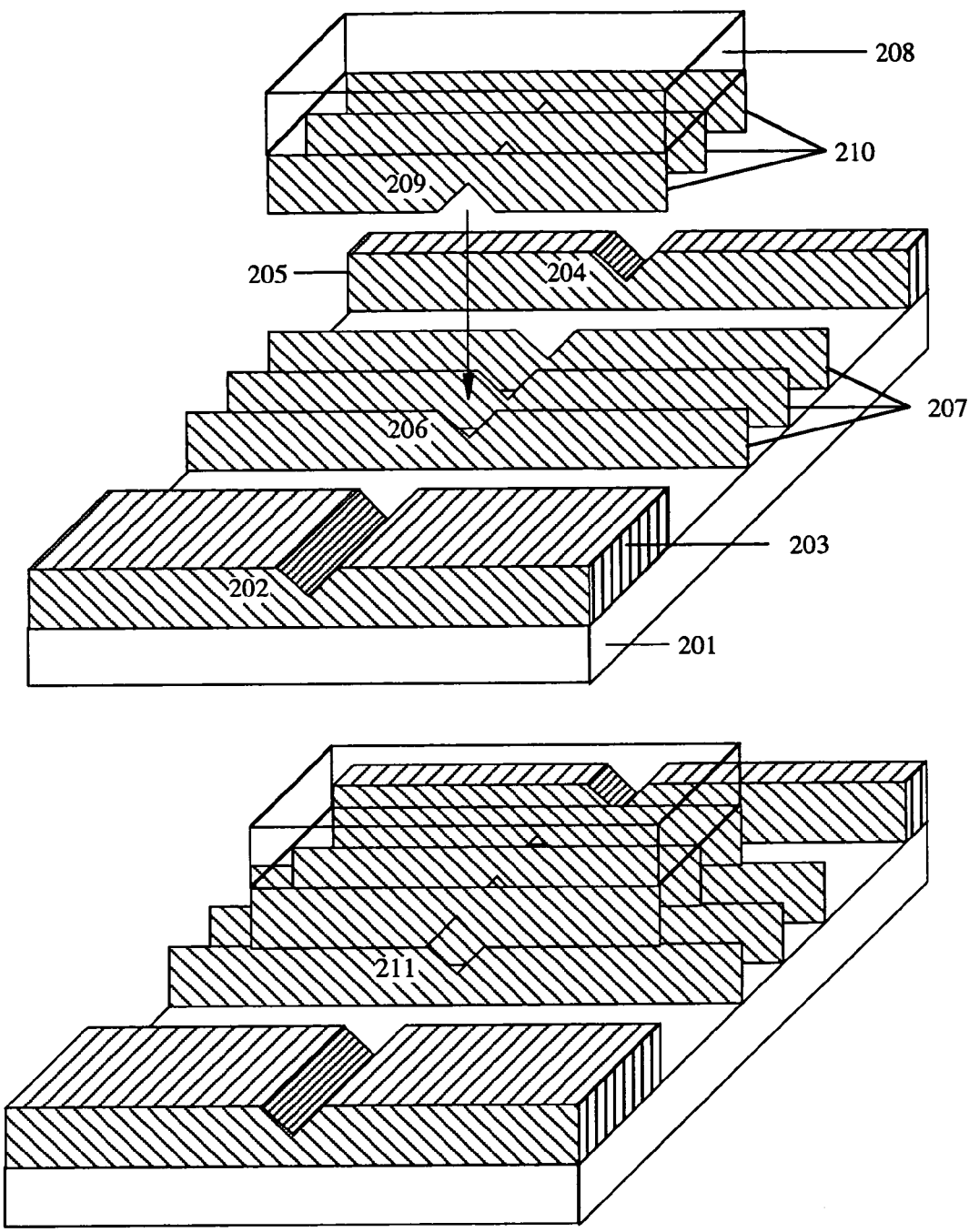
FIG. 2 shows construction of a microengineered nanospray system as a stacked assembly of two chips according to an embodiment of the present invention.

FIG. 2 illustrates the main features of the chip 108 used in the arrangement of FIG. 1. The chip is constructed from two separate substrates, each carrying microengineered features, which are arranged in a stacked assembly. The first substrate consists of a base 201 formed in insulating material and carrying a mechanical alignment feature for the input nanospray capillary corresponding to the feature 109 in FIG. 1, which may (for example, but not exclusively) consist of a groove 202 etched into a conducting or semiconducting block 203. In this non-claimed embodiment of the device, this substrate also carries an alignment feature for the capillary input to the mass spectrometer corresponding to the feature 110 in FIG. 1, which may again for example consist of a further groove 204 etched into a block of similar material 205. This substrate also carries a set of electrodes corresponding to part of the features 111 in FIG. 1 and consisting of grooves 206 etched into upright plates of similar material 207.

The second substrate again consists of a base 208 formed in insulating material, and carrying a further set of electrodes corresponding to a further part of the features 111 in corresponding to part of the features 111 in FIG. 1 and consisting of grooves 206 etched into upright plates of similar material 207.

The second substrate again consists of a base 208 formed in insulating material, and carrying a further set of electrodes corresponding to a further part of the features 111 in FIG. 1 and consisting of grooves 209 etched into upright plates of conducting or semiconducting material 210. When the two substrates are stacked together, the partial electrode sets combine to form complete diaphragm electrodes with closed pupils 211.

Using three such electrodes, a so-called 'einzel' or unipotential electrostatic lens is formed. This type of lens allows focusing of ions passing axially through the stack of electrodes in a simple and controlled manner, and hence allows the ion spray to be focused to present a concentrated stream of analyte ions which may be then introduced into the mass spectrometer.

It will be appreciated that the alignment grooves 202 and 204, and the electrode grooves 206 and 209, may all be defined by similar photolithographic processes, and may therefore be registered together. This aspect provides a solution to the first problem identified above in the Background to the Invention section, of constructing an accurately aligned set of mechanical features and electrodes. It will also be appreciated that the use of an insulating substrate that may be patterned with drain holes provides a solution to the problem of maintaining high voltages in a wet environment. The provision of these plurality of drain holes creates a percolated structure with a plurality of exit and entry apertures to assist in drainage or escape of non-required or non-desired gaseous constituents from the generated ion beam. Finally it will be appreciated that a stacked combination of partial electrodes provides a solution to the problem of forming diaphragm electrodes arranged normal to a substrate.

Figure 3:
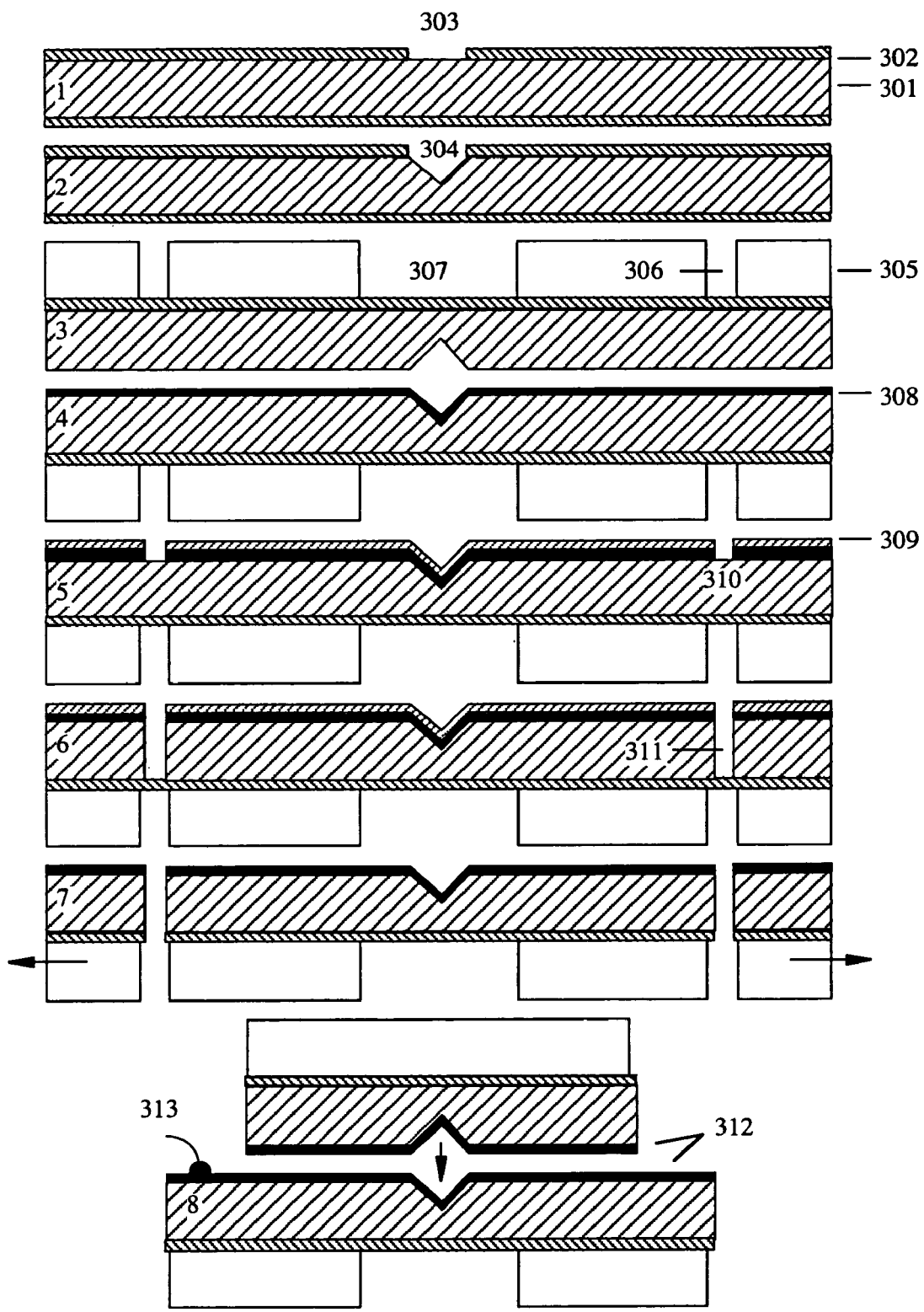
FIG. 3 is a process flow for construction of a microengineered nanospray chip according to an embodiment of the present invention.

It will be appreciated by those skilled in the art that a variety of materials and processes and may be used to realise structures similar to FIG. 2. FIG. 3 shows a process, which is intended to be exemplary rather than exclusive. The materials used are low cost, and only three lithographic steps are required. The process is based on crystalline silicon substrates on which plastic virtual substrates are subsequently formed. The individual process steps are indicated by a set of evolving wafer cross-sections containing typical features.

In step 1, a (100)-oriented silicon substrate 301 is first oxidised to form a $SiO_2$ layer 302 on both sides. The $SiO_2$ is patterned and etched to form a channel-shaped opening 303, by (for example) photolithography and reactive ion etching. In step 2, the underlying silicon substrate is anisotropically etched down (111) crystal planes to form a V-shaped groove 304. Commonly an etchant consisting of potassium hydroxide (KOH), water and isopropanol (IPA) may be used for this purpose. This step defines all capillary-mounting grooves and electrode pupils. The front side oxide is removed, and the wafer is turned over.

In step 3, the wafer is spin coated with a thick layer of the epoxy-based photoresist SU-8 305. This resist may be coated and exposed in layers of at least 0.5 mm thickness, has excellent adhesion, and is extremely rugged after curing, allowing it to be used as a virtual substrate material after processing. The resist is lithographically patterned to form a dicing groove 306 around each die, together with any drain holes 307 and gas inlets.

In step 4, the front side of the wafer is metallised to increase conductivity, typically with an adhesion layer of Cr metal and a further thicker layer of Au 308. In step 5, the front side of the wafer is coated in a photoresist 309. Since the wafer is nonplanar, an electrodeposited resist (such as the Shipley "Eagle" type) is used in preference to spin-coated resist for this step. The resist is patterned to define the outlines of all electrode and alignment blocks 310, and the pattern is transferred through the metal. In step 6, the pattern is transferred through the silicon wafer by deep reactive ion etching, to form deep separation features 311 between elements. The photoresist is then removed, and individual dies are separated in step 7.

In step 8, two dies are stacked together to form a complete nanospray chip, by soldering or bonding the metal layers 312 together. Alternatively, a conducting epoxy may be used for this step. The chip is mounted on a carrier circuit board, and wirebond connections 313 are made to appropriate features on the lower substrate.

It will be appreciated by those skilled in the art that a first alternative process is offered by forming the conducting alignment and electrode elements by electroplating a metal inside a mould, which may itself be formed by a sequence of patterning and etching steps. However, this alternative requires the separate formation of a mould, which is a laborious process.

It will also be appreciated by those skilled in the art that a second alternative process is offered by forming the alignment and electrode elements by sawing or otherwise eroding a conducting layer attached to an insulating substrate. The substrate bases may be also defined by sawing or by erosion, and the grooves may be formed, by partial sawing. However, this alternative offers less flexibility in the range of structures that may be created.

It will also be appreciated by those skilled in the art that a third alternative process is offered by forming the substrate bases from glass, which may be patterned by sawing or (in the case of a photosensitive glass) by photopatterning. However, these alternatives again offer less flexibility in the range of structure that may be created. It will be appreciated that regardless of their shortcomings that each of the mentioned alternatives may be considered useful in the context of the present invention for specific applications.

These and other alternatives for fabricating a chip according to the teaching of the invention will be understood by those skilled in the art as forming part of the process taught by the invention and it is not intended to limit the invention to any one specific process except as may be deemed necessary in the light of the dependent claims.

Figure 4:
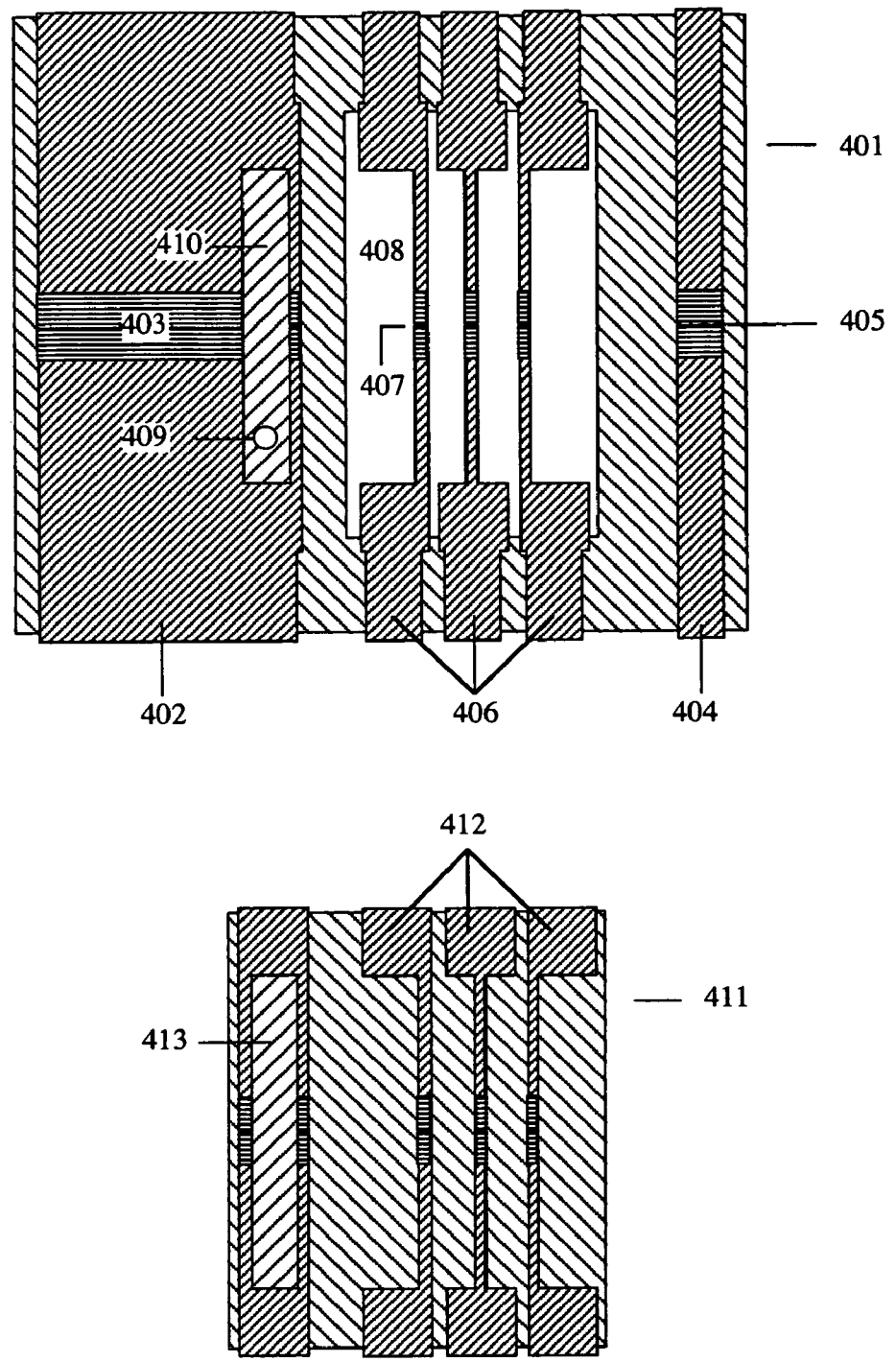
FIG. 4 shows the layout of a lower and an upper substrate of a microengineered nanospray chip according to an embodiment of the present invention.

FIG. 4 shows the layout of individual substrates that can be realised using the process of FIG. 3. The larger plastic substrate-base 401 carries a mounting block 402 for the nanospray input capillary, formed in etched, metallised silicon and having an etched alignment groove 403. The substrate carries a similar mounting block 404 for the mass spectrometer input capillary, with a similar etched alignment groove 405, and a set of partial electrodes 406 with etched grooves 407. The electrodes are widened at their extremities to assist in the stacked assembly and to allow bonding. A large hole 408 through the plastic substrate-base provides a drain, and a smaller hole 409 provides a channel for sheath gas to flow into an etched plenum chamber 410. The smaller plastic substrate-base 411 carries a further set of partial electrodes 412 and further features 413 defining the sheath gas plenum.

Figure 5:
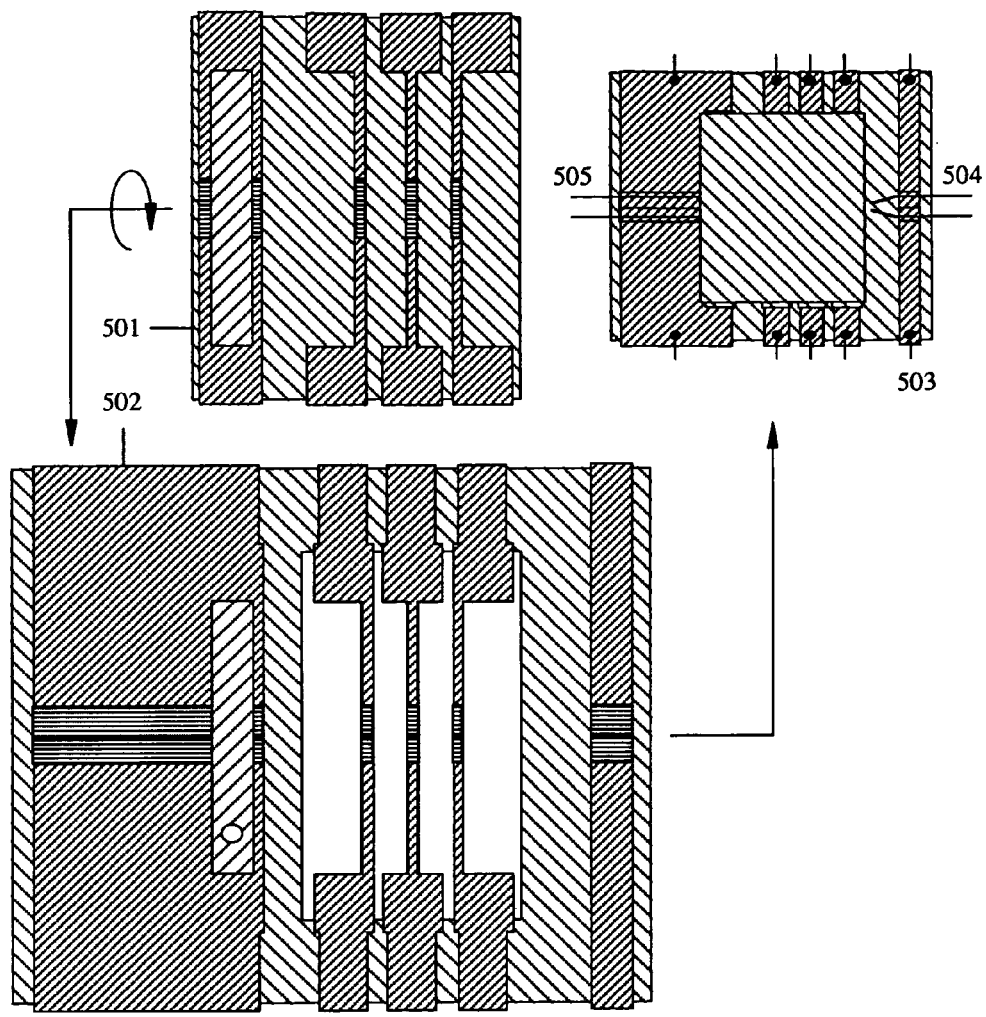
FIG. 5 shows an assembly of a microengineered nanospray chip according to an embodiment of the present invention.

FIG. 5 shows assembly. The smaller substrate 501 is inverted, aligned on top of the larger substrate 502, and the electrodes are bonded together. The device is mounted on an external printed circuit board, and wirebond connections 503 are attached to the alignment features and electrodes. The chip is aligned and connected electrically to the input capillary 504 of the mass spectrometer, and the nanospray capillary 505 is inserted into its input alignment feature and connected electrically. A stop may be provided on each capillary to ensure that it may only be inserted into its alignment groove for a fixed distance.

Figure 6:
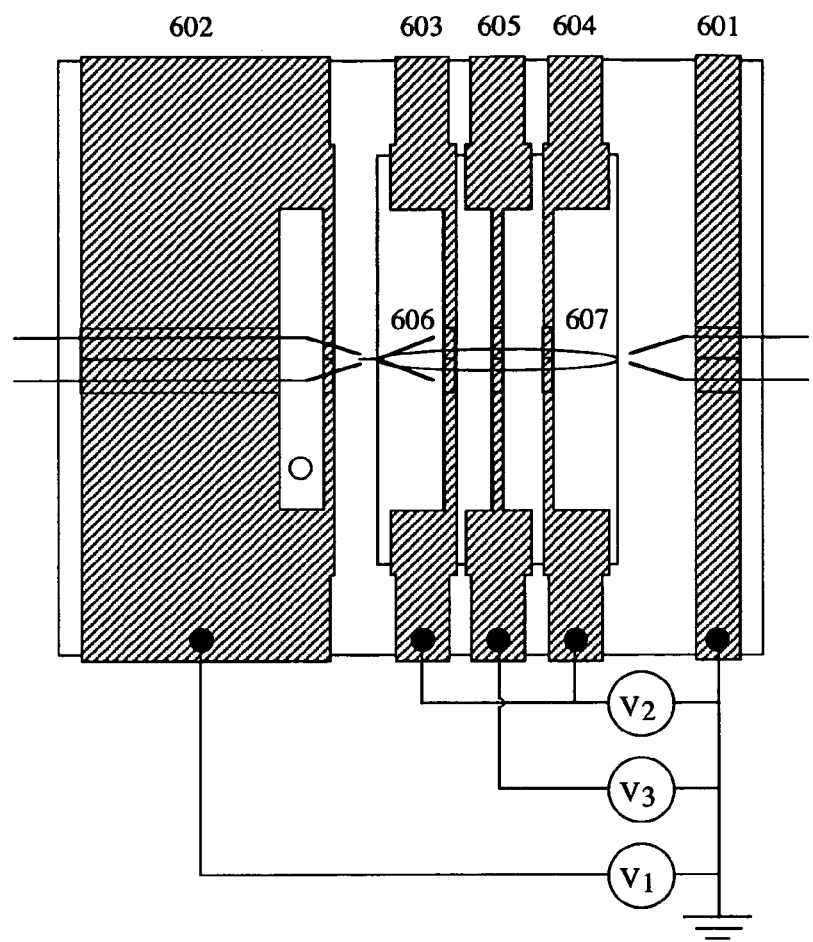
FIG. 6 shows electrostatic operation of a microengineered nanospray chip according to an embodiment of the present invention.

FIG. 6 shows electrostatic operation of the device. The capillary input to the mass spectrometer and its alignment feature 601 both are assumed to be at ground potential. Assuming that the nanospray capillary contains a conducting contact, a large DC voltage $V_1$ is applied to the nanospray capillary via its associated mount 602. Alternatively the voltage may be applied via a wire passing into the capillary. An intermediate voltage $V_2$ is applied to the outer electrodes 603, 604 of the lens element and a further voltage $V_3$ to the centre element 605. The spray 606 is emitted from a Taylor cone created at the exit of the nanospray capillary due to the potential difference $V_1$-$V_2$. The ion stream is focused onto the capillary input to the mass spectrometer 607 due to the action of the focus voltage $V_3$.

Figure 7:
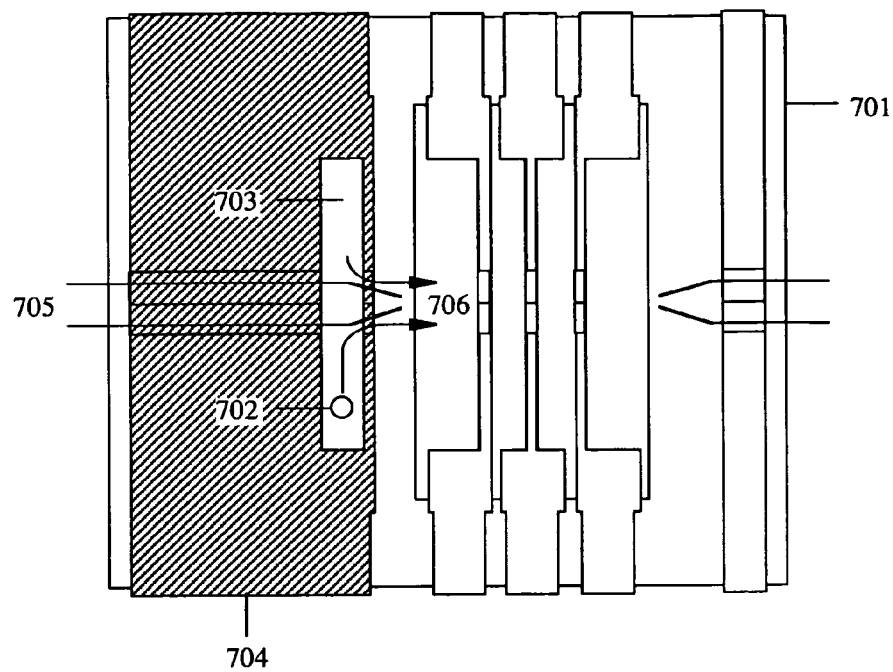
FIG. 7 shows operation of the sheath gas inlet of a microengineered electrospray chip according to an embodiment of the present invention.

FIG. 7 shows operation of the nebulizer gas inlet. Nebulizer gas is passed through the lower substrate-base 701 of the assembly via an inlet hole 702. The gas flows into a plenum 703 formed in the nanospray capillary mount 704. The gas leaks from the plenum around the capillary, because it does not fully seal the orifice formed by the grooves in the upper and lower nanospray capillary mount. However, the natural taper of the capillary 705 ensures that the majority of the leakage takes place in a forward axial direction 706, forming a sheath around the spray.

Figure 8:
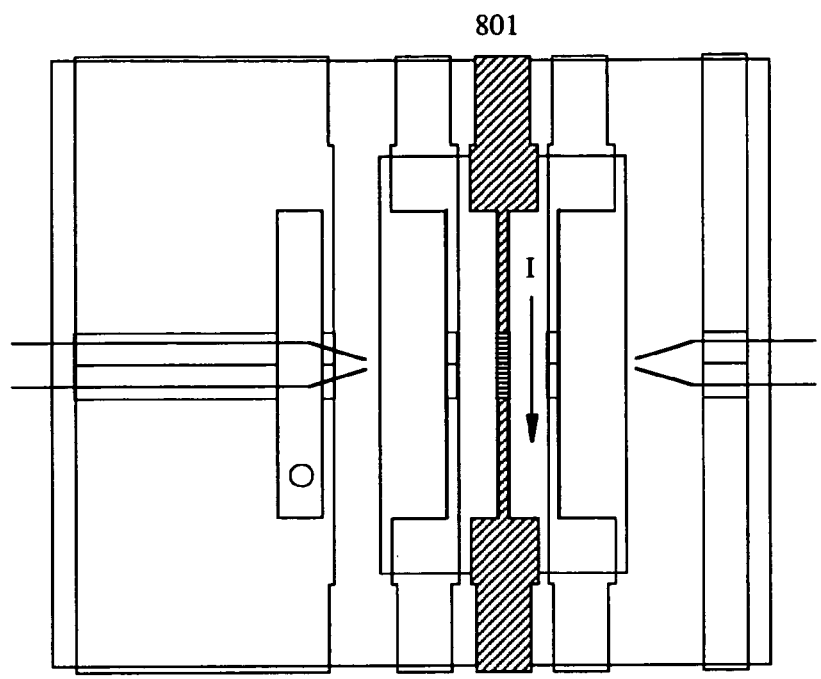
FIG. 8 shows thermal operation of a microengineered electrospray chip according to an embodiment of the present invention.
Figure 9:
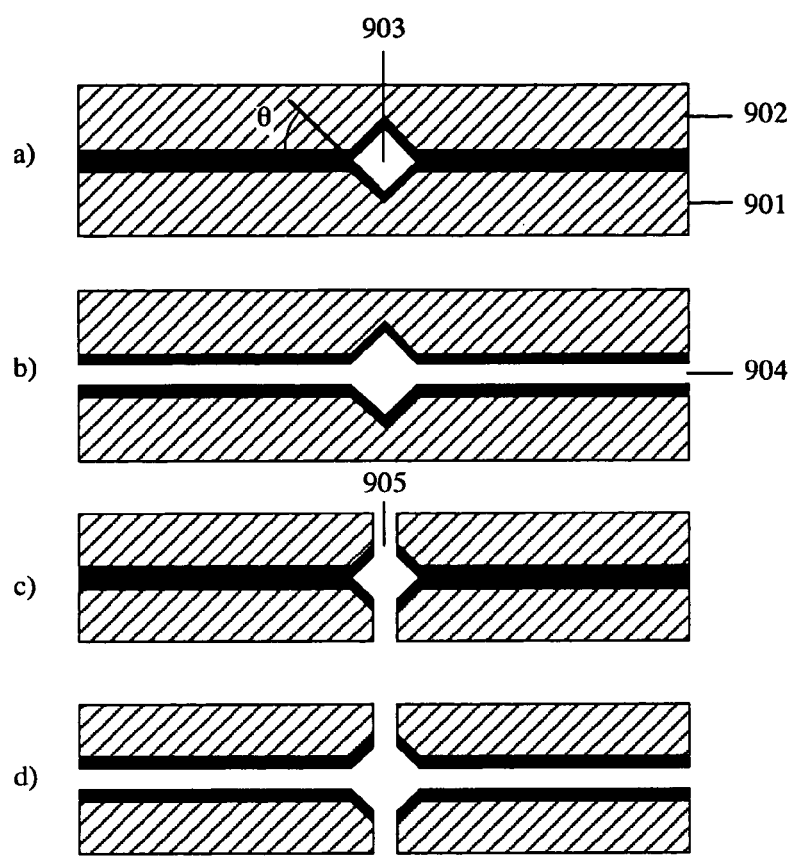
FIG. 9 shows electrode configurations realisable using a stacked electrode assembly with FIG. 9a) being a closed pupil arrangement, FIG. 9b) a horizontally split pupil, FIG. 9c) a vertically split pupil and FIG. 9d) a quadrant pupil arrangement.

FIG. 8 shows a mode of thermal operation. A current I is passed through one or more of the electrodes 801 to provide local heating, which may preferentially evaporate more volatile components in the spray such as a carrier solvent, thus enriching the analyte ion stream.

FIGS. 9*a*-9*d* shows different possible electrode cross sections. In the simplest realisation (FIG. 9*a*), the assembly of two plates 901 and 902 with grooves formed by anisotropic wet chemical etching will create electrodes with a diamond-shaped pupil 903. The edges of the pupil will be defined by the (111) crystal plane angle $\theta=\cos^{-1}(1/\sqrt{3})=54.73°$ of silicon. The size of the pupils may be controlled, by varying the width of the initial etched groove either continually or in discrete steps along the axis. It will be appreciated by those skilled in the art that other fabrication methods such as deep reactive ion etching may be used to form U-shaped alignment grooves and electrode grooves, which have greater inherent symmetry.

It will also be appreciated by those skilled in the art that the electrodes may be segmented horizontally using additional spacing 904 as shown in FIG. 9*b*, or segmented vertically using additional etching 905 as shown in FIG. 9*c*. Both methods of segmentation may be combined as shown in FIG. 9*d*. Segmented electrodes of this type may be used to provide one- or two-axis electrostatic deflection in addition to focusing. These additional degrees of freedom offer the potential to improve the separation of ions from neutrals, for example by inserting a bend or a dog-leg into the ion path that neutrals cannot follow.

It will also be appreciated that the ability to provide transverse electrostatic forces using segmented electrodes allows the spray to be deflected in a time-varying manner. If the spray is oscillated using for example a sinusoidal varying lateral force, a periodic perturbation may be induced in the spray flow. If the spatial frequency of this perturbation is chosen to coincide with the spatial frequency of Rayleigh instability in the flow pattern, the flow will be encouraged to fragment into droplets, thus promoting nebulisation.

What has been described herein is a microengineered implemented nanospray device which is interfaced between a fluid source and a mass spectrometer. As was discussed previously such a device addresses the problems of constructing an accurately aligned set of mechanical features and electrodes, allows for a maintaining high voltages in a wet environment and provides a solution to the problem of forming diaphragm electrodes arranged normal to a substrate.

In the embodiments of FIGS. 1 to 9 the device was described as being physically coupled to both the fluid source and the mass spectrometer through use of capillaries at both the input and output of the device. In such a way it was useful for operation with mass spectrometers that use a capillary input. Using capillary inputs to mass spectrometers requires an accurate presentation of a generated ion beam to the capillary input and in this context it is necessary for the device of the invention to enable an alignment of the formed ion spray with the input capillary to the mass spectrometer device.

However it has been found that a device in accordance with the teaching of the invention can be used successfully with mass spectrometer devices that do not use capillary inputs, and in such arrangements the use of and requirement for the capillary at the output of the device is obviated. Such an embodiment will now be described with reference to FIGS. 10 to 13 where a generated ion beam exits the nanospray ionisation device prior to being received into the mass spectrometer, i.e. there is no direct physical coupling between the exit of the device and the entrance to the mass spectrometer as was provided through the capillary 106.

Figure 10:
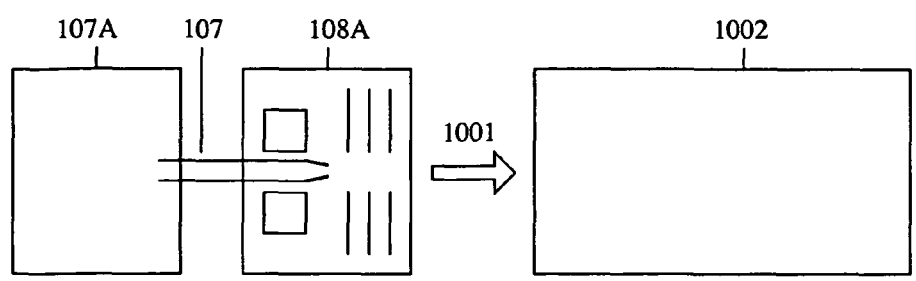
FIG. 10 shows an alternative to FIG. 1, in which the output from the microengineered nanospray system is not directly coupled to the mass spectrometer system.

As shown in FIG. 10, a fluid source 107A is directly coupled to an ionisation device 108A through use of a capillary 107. A generated ion beam 1001, exits the device 108A prior to being received into the mass spectrometer 1002. There is no direct physical coupling between the exit and the input required as a general co-location of the output from the nanospray device 108A with the input to the mass spectrometer provides sufficient coupling for the generated nanospray 1001 to be introduced into the mass spectrometer. In this context a device according to the teaching of the invention could be used with mass spectrometers having non-capillary inputs. Within the context of the present specification the phrase "non-capillary" will be understood as having dimensions greater than that of a capillary or having a non-tubular geometry.

Figure 11:
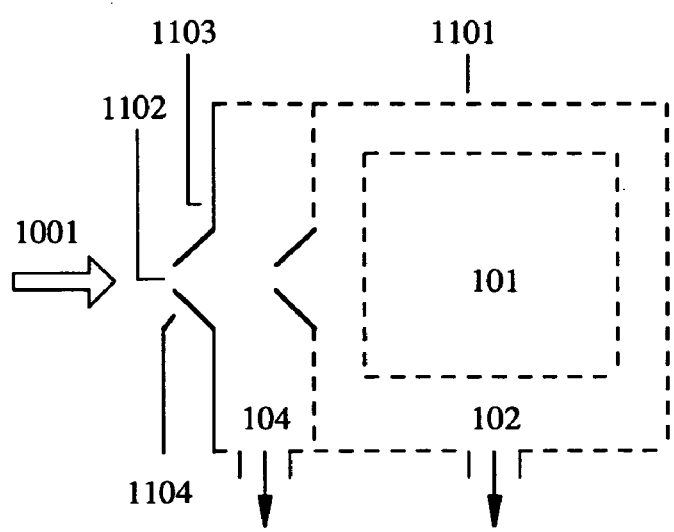
FIG. 11 shows alternative details of the inlet of a mass spectrometer system.

FIG. 11 shows a portion of an entrance aperture 1102 of a mass spectrometer 1101 that could be used within the context of the system of FIG. 10. In this embodiment the entrance aperture 1102 is set forward from a front surface 1103 of the mass spectrometer. Side walls 1104 extending outwardly from the front surface of the mass spectrometer are arranged to slope towards one another to define the aperture region of the entrance aperture. By applying a suitable voltage to these side walls it is possible to selectively direct the ion beam 1001 into the entrance aperture as opposed to onto the side walls or front surface of the mass spectrometer. Such an arrangement is conventionally referred to as a sampling cone.

Figure 12:
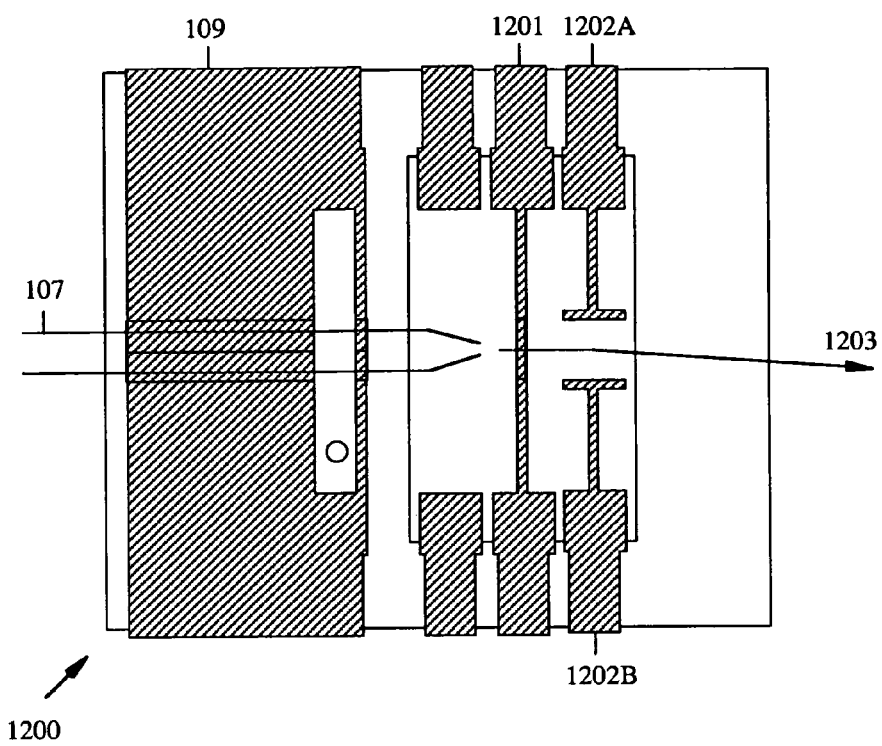
FIG. 12 shows an alternative to FIG. 4, in which the output capillary alignment feature is omitted from the microengineered nanospray bench and deflection electrodes are provided.

FIG. 12 shows in plan view internal components of a nanospray device 1200 according to the teaching of the invention. Where components have already been described with reference to FIGS. 1 to 9, the same reference numerals will be used. Similarly to the embodiment described with reference to FIGS. 1 to 9, this embodiment also includes alignment features 109 for receiving an entrance capillary 107 from a fluid source. In this embodiment, a single electrode 1201 is provided to extract an ion spray from the capillary tip. A further pair of deflector electrodes 1202A, 1202B are provided, to deflect the resulting ions into an off-axis spray. Provision of the deflection field requires a voltage source of a few 100 volts, floating near the voltage of the extraction electrode 1201. By passing the generated ion spray passed the deflector electrodes, ions within the ion spray will be affected by the generated field and will be directed in a new path direction 1203, with other non-ionised molecules continuing in their original path. The use of ion deflection may therefore reduce contamination of the inlet to the mass spectrometer, and also to correct for slight misalignment between the ion source and the mass spectrometer inlet.

In this embodiment, the specifics of ion focusing that was described with reference to FIGS. 1 to 9 has been omitted. However, it will be apparent that additional electrodes may be included to combine ion focusing and deflection as required. Typically where included, the ion focusing electrodes will be provided prior to the ion deflection electrodes to enable a focusing of the ion beam prior to it being deflected.

Figure 13:
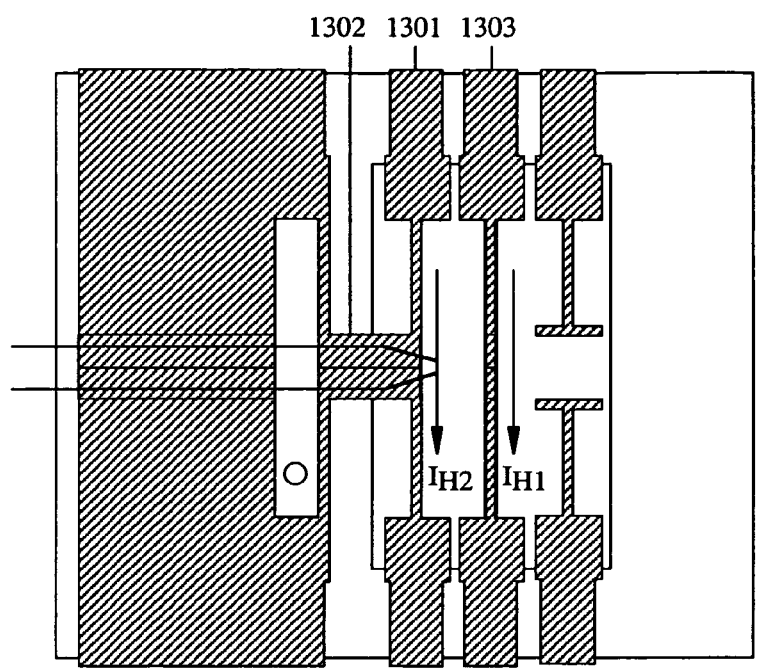
FIG. 13 shows an alternative to FIG. 12, in which the nebuliser is arranged as a heated tube, concentric to the nanospray capillary.

FIG. 13 shows a further modification to the arrangement of FIG. 12 which provides for a heating of the ion beam. A first arrangement includes an additional heater element 1301 which is arranged along the ion path to assist in desolvation of the generated ion beam. This arrangement provides a heated nebuliser for situations where an unheated nebuliser may fail to achieve sufficient desolvation. By providing the nebuliser, desirably as a tubular element 1302, it is possible to pass the nebulizer gas, the use of which was described previously with respect to FIG. 7, through this heater element and then stimulate additional desolvation. The heated nebuliser gas is directed onto the tip of the capillary and stimulates desolvation. In this case, a second power supply (floating at a much higher voltage) is required to provide the heater current $I_{H2}$.

In this illustration of an embodiment according to the teaching of the invention, the specifics of ion focusing has again been omitted. However, it will be apparent that again additional electrodes may be combined as required to include ion focusing and/or deflection.

One of more of these additional electrodes could be used in combination with the heated nebuliser 1301/1302, and for example as shown in FIG. 13 a second heater could also be provided within the device. In the arrangement of FIG. 13 an extraction electrode 1303 is provided which is coupled to a current $I_{H1}$ so as to achieve a heating of that electrode. By providing an aperture in that extraction electrode the generated ion beam will pass through the heated electrode and will therefore also experience a heating. To assist in the decontamination of the ion beam, one or more apertures could be provided in the roof of the aperture formed in the extraction electrode to assist in the escape of the by-product of the heating. Of course it will be appreciated that the presence of two heating components within the device is an optional feature, and that one or more of the two described could suffice for certain applications.

Therefore while advantageous embodiments have been described it will be appreciated that certain integers and components are used to illustrate exemplary embodiments and it is not intended to limit the invention in any way except as may be deemed necessary in the light of the appended claims. Furthermore where the invention is described with reference to specific figures it will be appreciated that components or features of one figure can be freely interchanged with those of other figures without departing from the scope of the invention.

Within the context of the present invention the term microengineered or microengineering is intended to define the fabrication of three dimensional structures and devices with dimensions in the order of microns. It combines the technologies of microelectronics and micromachining. Microelectronics allows the fabrication of integrated circuits from silicon wafers whereas micromachining is the production of three-dimensional structures, primarily from silicon wafers. This may be achieved by removal of material from microengineering of wafers, and will be well known to the person skilled in the art. The techniques may be divided into those related to the removal of material and those pertaining to the deposition or addition of material to the wafer. Examples of the former include:

1) wet chemical etching (anisotropic and isotropic);
2) electrochemical or photo assisted electrochemical etching;
3) dry plasma or reactive ion etching;
4) ion beam milling;
5) laser machining; and,
6) eximer laser machining.

Whereas examples of the latter include:

1) evaporation;
2) thick film deposition;
3) sputtering;
4) electroplating;
5) electroforming;
6) moulding;
7) chemical vapour deposition (CVD); and.
8) epitaxy.

These techniques can be combined with wafer bonding to produce complex three-dimensional structures, examples of which are the devices provided by the present invention.

The words comprises/comprising when used in this specification are to specify the presence of stated features, integers, steps or components but does not preclude the presence or addition of one or more other features, integers, steps, components or groups thereof.

REFERENCES

Gaskell S. J. "Electrospray: Principles and practice" J. Mass Spect. 32, 677-688 (1997)

Abian J. "The coupling of gas and liquid chromatography with mass spectrometry" J. Mass Spectrom. 34, 157-168 (1999)

Duffin K. L., Wachs T., Henion J. D. "Atmospheric-pressure ion-sampling system for liquid-chromatography mass-spectrometry analyses on a benchtop mass-spectrometer" Anal. Chem. 64, 61-68 (1992)

Lee E. D., Henion J. D. "Thermally-assisted electrospray interface for liquid-chromatography mass-spectrometry" Rapid Comm. in Mass Spect. 6, 727-733 (1992)

Huggins T. G., Henion J. D. "Capillary electrophoresis mass-spectrometry determination of inorganic ions using an ion spray-sheath flow interface electrophoresis"14, 531-539 (1993)

Hirabayashi A., de la Mora J. F. "Charged droplet formation in sonic spray" Int. J. Mass Spect. 175, 277-282 (1998)

Li G., Yin H. "Mass spectrometer electrospray ionization" U.S. Pat. No. 6,462,337

Wilm M., Mann M. "Analytical properties of the nanoelectrospray ion source" Anal. Chem. 68, 1-8 (1996)

Ramsey R., Ramsey J. "Generating electrospray from microchip devices using electro-osmotic pumping" Anal. Chem. 69, 1174-1178 (1997)

Licklider L., Wang X. Q., Desai A., Tai Y. C., Lee T. D. "A micromachined chip-based electrospray source for mass spectrometry" Anal Chem. 72, 367-75 (2000)

Svedberg M., Petterson A., Nilsson S., Bergquist J., Nyholm L., Nikolajeff F., Markides K. "Sheathless electrospray from polymer microchips" Anal Chem. 75, 3934-3940 (2003)

Le Gac S., Arscott S., Rolando C. "A planar microfabricated nanoelectrospray emitter tip based on a capillary slot" Electrophoresis 24, 3640-3647 (2003)

Kameoka J., Orth R., Czaplewski D., Wachs T., Craighead H. G. "An electrospray ionization source for integration with microfluidics" Anal. Chem. 74, 5897-5901 (2002)

Schultz G. A., Corso T. N., Prosser S. J., Zhang S. "A fully integrated monolithic microchip electrospray device for mass spectrometry" Anal. Chem. 72, 4058-4063 (2000)

Griss P., Melin J., Sjödahl J., Roeraade J., Stemme G. "Development of micromachined hollow tips for protein analysis based on nanoelectrospray ionization mass spectrometry" J. Micromech. Microeng. 12, 682-687 (2002)

Bean K. E. "Anisotropic etching of silicon" IEEE Trans. Electron Devices ED-25, 1185-1193 (1978)

Hynes A. M., Ashraf H., Bhardwaj J. K., Hopkins J., Johnston I., Shepherd J. N. "Recent advances in silicon etching for MEMS using the ASE™ process" Sensors and Actuators 74, 13-17 (1999)

Lorenz H., Despont M., Fahrni N., LaBianca N., Renaud P., Vettinger P. "SU-8: a low-cost negative resist for MEMS" J. Micromech. Microeng. 7, 121-124 (1997)

The invention claimed is:

1. A microengineered ionisation device provided on a single chip for coupling between a fluid source and a mass spectrometer, the device, in use, providing for a generation of an ion beam from a fluid originating in the fluid source, the generated ion beam being subsequently directed into the mass spectrometer, the device including:

a) an input having an alignment feature for cooperating with a capillary input from the fluid source so as to provide for a direct coupling of the source to the input of the device, the capillary input transporting the fluid from the source to the device where it exits as a spray from a tip of the capillary input into the device;
b) an output from which the generated ion beam exits the device;
c) an orifice defining an ion path between the capillary input and the output;
d) at least one conducting electrode provided in an orientation substantially perpendicular to the ion path, and wherein each of the input, the alignment feature, the orifice, the at least one electrode and the output are integrally formed in the chip and the generated ion beam exits the device prior to being directed into the mass spectrometer.

2. The device as claimed in claim 1 wherein the device includes a heated nebuliser provided adjacent to the tip of the capillary input and configured to provide for a heating of a gas flowing over the capillary input.

3. The device as claimed in claim 2 wherein the heated nebuliser is provided as a concentric tube about the tip of the capillary input.

4. The device as claimed in any claim 1 including a pair of deflector electrodes, the deflector electrodes being arranged to deflect the generated ion spray beam off-axis.

5. The device as claimed in claim 4 wherein the ion path defined by the orifice is a nonlinear path such that the output from the device and the input capillary are off-axis.

6. The device as claimed in claim 4 wherein the deflector electrodes provide for a discriminative deflection of ions contained within the ion beam off-axis while non-ionised particles are maintained in their original path.

7. The device as claimed in claim 1 including a heated electrode provided along the ion path, the heated electrode providing for desolvation of the generated ion beam.

8. The device as claimed in claim 7 wherein the heated electrode is provided as a tubular electrode through which the ion beam passes.

9. The device as claimed in claim 7 wherein the second substrate has provided thereon at least one conducting electrode with a grooved upright edge arranged normal to the substrate.

10. The device as claimed in claim 9 wherein on stacking the first and second substrates relative to one another the at least one electrodes provided on the first and second substrates form a contiguous electrode and the electrode grooves combine to form orifices.

11. The device as claimed in any claim 1 wherein the chip is constructed from two substrates, the substrates being combined in a stack configuration so as to form the chip.

12. The device as claimed in claim 11 wherein each of the two substrates are provided with an insulating base, the substrates being stacked relative to one another such that the resultant chip has an insulating portion on an outer surface thereof.

13. The device as claimed in claim 12, in which at least a first substrate base contains at least one inlet hole for gases and a plenum chamber surrounding the capillary input.

14. The device as claimed in claim 13, in which the plenum chamber is arranged to create an axial flow of gas arranged as a sheath to the spray.

15. The device as claimed in claim 14 wherein at least part of the plenum chamber is heatable.

16. The device as claimed in claim 12 wherein the insulating base is formed in a photopatternable polymer.

17. The device as claimed in claim 16 in which a substrate-base perimeter, drain holes and gas inlets are defined by photopatterning.

18. The device as claimed in claim 12, in which the substrate-bases are formed in glass.

19. The device as claimed in claim 18 in which the glass is photopatternable.

20. The device as claimed in claim 11 wherein each of the two substrates are formed with individual features, the features being configured such that when the two substrates are brought together the resultant combination of features define the alignment feature, the orifice and the at least one electrode.

21. The device as claimed in claim 20 wherein a first substrate defines a first grooved alignment feature for the capillary input, the substrate additionally having provided thereon the at least one conducting electrode with a grooved upright edge arranged normal to the substrate.

22. The device as claim in claim 21, in which the electrodes, grooves or substrate-bases are formed by sawing.

23. The device as claimed in claim 1 where the capillary input is a nanospray capillary input configured to provide a fluid derivable from a liquid chromatography system or from a capillary electrophoresis system.

24. The device as claimed in claim 1 wherein the electrode nearest to the input capillary is used first to create a Taylor cone and then to extract ions from liquid contained in the input capillary.

25. The device as claimed in claim 1 including at least two electrodes and wherein at least a second electrode is used to focus ions onto the output.

26. The device as claimed in claim 1 where at least one electrode is electrically heated and used to remove solvent preferentially.

27. The device as claimed in claim 1 wherein at least a portion of the device is heatable.

28. The device as claimed in claim 1, where at least one electrode is segmented and used to provide a deflecting lateral electric field to assist in separating ions from neutrals.

29. The device as claimed in claim 28, where the deflecting lateral field is time varying and used to promote nebulisation.

30. The device as claimed in claim 1 wherein the chip contains at least one drain hole for fluids.

31. The device as claimed in claim 1, in which the alignment feature and electrodes are formed in a semiconductor material.

32. The device as claimed in claim 31, in which the semiconductor is silicon.

33. The device as claimed in claim 31, in which the semiconductor is grooved by anisotropic wet chemical etching down crystal planes.

34. The device as claimed in claim 31, in which the semiconductor is grooved by deep reactive ion etching.

35. The device as claimed in claim 31, in which either the alignment feature or the electrodes are formed using deep reactive ion etching.

36. The device as claimed in claim 1, in which the alignment features and electrodes are formed in a metal.

37. The device as claimed in claim 36, in which the metal is deposited by electroplating.

38. The device of claim 1 wherein the source is an nanospray ionisation source, the device being a nanospray ionisation device.

39. An integrated package including a source having a capillary needle at an output thereof, a mass spectrometer having an input and a ionisation device as claimed in any preceding claim provided between the source and the mass spectrometer, the alignment features of the device providing connection ports for the capillary needle so as to enable a fluid originating from the source to be ionised and passed to the mass spectrometer.

40. The package of claim 39 wherein the mass spectrometer is provided with a sampling cone, the sampling cone serving to direct an ion beam generated within and exiting from the ionisation device into the mass spectrometer.

* * * * *